United States Patent [19]
Merten et al.

[11] 3,966,683
[45] June 29, 1976

[54] PROCESS FOR THE PREPARATION OF COMPOUNDS WHICH CONTAIN HYDANTOIN GROUPS

[75] Inventors: Rudolf Merten, Leverkusen; Jürgen Lewalter, Cologne; Wilfried Zecher, Leverkusen, all of Germany

[73] Assignee: Bayer Aktiengesellschaft, Germany

[22] Filed: Aug. 1, 1974

[21] Appl. No.: 493,520

Related U.S. Application Data

[63] Continuation-in-part of Ser. No. 457,852, April 4, 1974, abandoned.

[30] Foreign Application Priority Data
Apr. 11, 1973   Germany............................ 2318198

[52] U.S. Cl..................... 260/77.5 AC; 260/33.4 R; 260/77.5 AB; 260/77.5 R; 260/309.5; 260/858; 260/859 R; 260/DIG. 34
[51] Int. Cl.² ................. C08G 18/24; C08G 18/26; C08G 18/18; C08G 18/34

[58] Field of Search................ 260/77.5 R, DIG. 34, 260/77.5 AB, 77.5 AC

[56] References Cited
UNITED STATES PATENTS

| | | | |
|---|---|---|---|
| 2,829,157 | 4/1958 | McKinney.................... | 260/DIG. 34 |
| 3,296,208 | 1/1967 | Rogers........................ | 260/DIG. 34 |
| 3,397,253 | 8/1968 | Merten et al. ............... | 260/DIG. 34 |
| 3,642,524 | 2/1972 | Merten et al. ............... | 260/DIG. 34 |
| 3,676,455 | 7/1972 | Haug et al. .................. | 260/DIG. 34 |
| 3,839,354 | 10/1974 | Habermeier et al.......... | 260/2.5 AB |

*Primary Examiner*—H.S. Cockeram
*Attorney, Agent, or Firm*—Connolly and Hutz

[57] ABSTRACT

A process for preparing compounds which contain hydantoin groups, which is characterized in that compounds which contain isocyanate or isothiocyanate groups are reacted with compounds which contain an α-halocarboxylic acid group or derivatives thereof at least once in the molecule.

13 Claims, No Drawings

PROCESS FOR THE PREPARATION OF COMPOUNDS WHICH CONTAIN HYDANTOIN GROUPS

This is a continuation-in-part of application Ser. No. 457,852, filed Apr. 4, 1974, now abandoned.

It is known to prepare polyhydantoins by reacting glycine ester derivatives which are at least difunctional with polyisocyanates (see French patent specification No. 1,484,694). This method of formation of polyhydantoins may be represented by the following schematic and very simplified reaction equation:

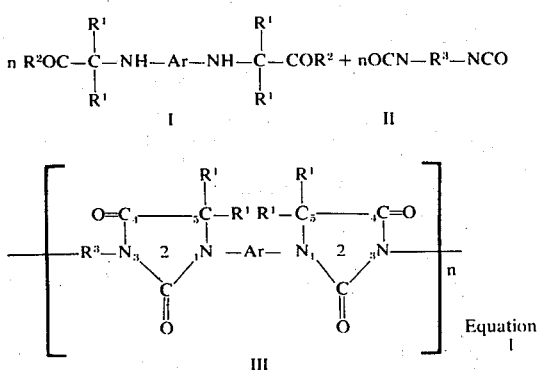

Equation 1

In this reaction equation, the symbols $R^1$ represent, independently of each other, hydrogen or an alkyl radical which preferably contains 1 to 4 carbon atoms, $R^2$ denotes hydroxyl, amino, alkylamino, dialkylamino, alkoxy or aroxy, the alkyl radicals preferably containing 1 – 4 carbon atoms and the aryl radical preferably 6 – 10 carbon atoms, Ar denotes an aromatic radical and $R^3$ denotes the organic radical of a diisocyanate.

The reaction may also be carried out with polyfunctional starting materials, i.e. with glycine ester derivatives which contain more than 2 glycine ester functions and polyisocyanates which contain more than 2 isocyanate groups. In that case, branched molecules are formed. Owing to the method of preparation, the hydantoin rings in these products are always arranged in a 3-1-1-3 linkage as shown in Formula III, i.e. they are always arranged in mirror image formation with respect to the connecting radicals $R^3$ and Ar.

This invention relates to a new process for preparing compounds which contain hydantoin groups, which is characterised in that compounds which contain isocyanate or isothiocyanate groups are reacted with compounds which contain an α-halocarboxylic acid group or derivatives thereof at least once in the molecule.

The starting materials which contain isocyanate groups are preferably diisocyanates or polyisocyanates and the reactants which contain α-halocarboxylic acids or derivative groups are preferably α-halogenated carboxylic acids or derivatives thereof.

The reaction may be represented by the following reaction scheme in which a diisocyanate is used as example:

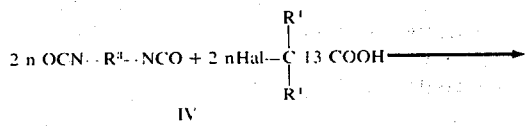

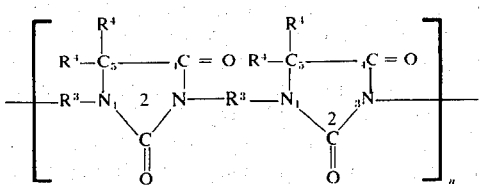

+2nHHal + 2nCO₂   Equation 2

In the structural element of formula V, the hydantoin rings are shown in the 3-1-3-1 linkage. This is intended to convey that the rings need not necessarily be arranged in mirror image formation as in the structural unit of formula III. The rings may all be similarly arranged or their arrangement may be statistical, depending on the reactivity of the reactants and the reaction conditions.

The process may in principle be carried out with any known compounds which contain isocyanate or isothiocyanate groups. If monoisocyanates or monoisothiocyanates and a compound which contains only one α-halocarboxylic acid group are used, the compounds obtained have only one hydantoin ring, whereas if polyiso(thio)cyanates and/or compounds which contain several α-halocarboxylic acid groups are used, then the products obtained are linear or branched, oligomeric or polymeric substances, depending on the proportions in which the reactants are used, with hydantoin rings as connecting members. In the case of di- and polyiso(thio)cyanates, the chain is then continued through the nitrogen atoms in the 1- and 3-position or if compounds with several α-halocarboxylic acid groups are used, then it may also be continued through the C-atoms in the 5-position. The combination of these two possible forms of cross-linking may be continued to the point where cross-linked high molecular weight substances are obtained. The stoichiometric reaction between a diisocyanate and an α-halocarboxylic acid represented in equation 2 serves as an example of the synthesis of a linear polymer.

Mono- and polyiso(thio)cyanates suitable for the process are compounds of the general formulae $$R^3(-NCO)_z \text{ or } R^3(-NCS)_z;$$

in which $R^3$ represents an optionally substituted aliphatic radical containing 1 – 20 carbon atoms, an aromatic radical containing 5 – 12 carbon atoms, a cycloaliphatic radical containing 5 – 12 carbon atoms, an aliphatic aromatic radical containing 6 – 20 carbon atoms and an aromatic or cycloaliphatic heterocyclic radical which contains or is substituted by hetero atoms such as N, O or S and contains 5 – 12 ring atoms. Aliphatic radicals which contain 2 – 6 carbon atoms and phenyl-, tolyl-, naphthyl-, diphenylmethane- and diphenyl ether radicals are particularly preferred, z is an integer of from 1 to 4 and in particular 2 to 3.

The monoisocyanates used for this invention are aliphatic or aromatic compounds which contain one NCO group in the molecule and which may be substituted by hetero atoms, e.g. alkylisocyanates such as ethyl-, methyl-, butyl-, dodecyl-, stearyl-, isopropyl- or nonyl isocyanate, aromatic monoisocyanates which are optionally substituted such as phenyl-, tolyl-, isopropyl-, nonyl-, nitro-, alkoxy-, chloro-, dichloro-, trichloro-, tetrachloro-, pentachloro-, benzyl- or bromophenyl isocyanate, isocyanatobenzoic, isocyanatophthalic or isocyanatoisophthalic acid esters or isocyanatobenzonitrile, cycloaliphatic isocyanates such as cyclohexylisocyanate or unsaturated isocyanates such as allyl, oleyl or cyclohexenyl isocyanate.

The isocyanates used as starting components according to the invention may also be aliphatic, cycloaliphatic, araliphatic, aromatic or heterocyclic polyisocyanates (see Annalen, 562, pages 75 to 136), for example ethylene diisocyanates, tetramethylene-1,4-diisocyanate, hexamethylene -1,6-diisocyanate, dodecane-1,12-diisocyanate, cyclobutane-1,3-diisocyanate, cyclohexane-1,3- and -1,4-diisocyanate and any mixtures of these isomers, 1-isocyanato-3,3,5-trimethyl-5-isocyanatomethylcyclohexane (U.S. Pat. No. 3,401,190), hexahydrotolylene-2,4- and -2,6-diisocyanate and any mixtures of these isomers, hexahydrophenylene-1,3- and/or 1,4-diisocyanate, perhydrodiphenylmethane-2,4'- and/or -4,4'-diisocyanate, phenylene-1,3- and -1,4-diisocyanate, tolylene-2,4- and -2,6-diisocyanate and any mixtures of these isomers, diphenylmethane-2,4'- and/or 4,4'-diisocyanate, naphthylene-1,5-diisocyanate, triphenylmethane-4,4',-4''-triisocyanate, polyphenylpolymethylenepolyisocyanates which can be obtained by aniline-formaldehyde condensation followed by phosgenation and which have been described, for example in British patent specification Nos. 874,430 and 848,671, perchlorinated aryl polyisocyanates such as those described e.g. in U.S. Pat. No. 3,277,138, polyisocyanates which contain carbodiimide groups as described in U.S. Pat. No. 3,152,162, the diisocyanates described in U.S. Pat. No. 3,492,330, polyisocyanates which contain allophanate groups as described e.g. in British patent specification Nos. 994,890, 1,288,688 and 1.308,652, polyisocyanates which contain isocyanurate groups as described e.g. in British patent specification Nos. 843,841, 1,091,949, 1,267,011, 1,304,836 and 1,305,036, polyisocyanates which contain urethane groups as described e.g. in British patent specification No. 1,302,201 or in U.S. Pat. No. 3,394,164, polyisocyanates which contain acylated urea groups according to U.S. Pat. 3,517,039, a polyisocyanates which contain biuret groups as described e.g. in U.S. Pat. No. 3,124,605, and in British patent specification Nos. 889,050 and 1,308,652, polyisocyanates prepared by telomerisation reactions as described e.g. in U.S. Pat. No. 3,654,106, polyisocyanates which contain ester groups such as those mentioned e.g. in British patent specification Nos. 956,474, 1,072,956, 1,086,404 and in U.S. Pat. No. 3,567,763 and reaction products of the above mentioned isocyanates with acetals according to U.S. Pat. No. 3,120,502.

The distillation residues obtained from the commercial production of isocyanates and still containing isocyanate groups may also be used, optionally dissolved in one or more of the above mentioned polyisocyanates. Any mixtures of the above mentioned polyisocyanates may also be used.

It is preferred to use commercially readily available mixtures of tolylene diisocyanates, m-phenylene diisocyanate, phosgenated condensates of aniline and formaldehyde which have a polyphenylene-methylene structure and the symmetrical compounds 4,4'-diisocyanatodiphenylmethane, 4,4'-diisocyanatodiphenylether, p-phenylene diisocyanate and 4,4'-diisocyanatodiphenyl-dimethylmethane and analogous hydroaromatic diisocyanates as well as hexamethylene diisocyanate.

The isocyanates may be used in the free form of partly or completely in the form of masked isocyanates which react as the corresponding free isocyanates under the given reaction conditions and have been obtained by reaction with compounds which contain active hydrogen atoms.

The masked isocyanate compounds used are preferably carbamic acid esters which can be obtained from aromatic and aliphatic monohydroxy and polyhydroxy compounds, e.g. carbamic acid esters of the general formulae

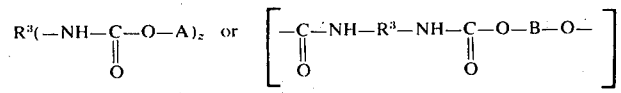

in which $R^3$ denotes the organic radical of an iso(thio)-cyanate, and the organic radical A of a monohydroxy compound or the organic residue B of a difunctional or trifunctional hydroxy compound denotes an aliphatic radical containing 1 – 10 carbon atoms, a cycloaliphatic radical containing 5 – 10 carbon atoms, an aliphatic aromatic radical containing 6 – 12 carbon atoms or an aromatic radical containing 5 – 12 carbon atoms, any of which radicals may be substituted; z denotes an integer of from 1 – 4, preferably 2 to 3.

Suitable examples include the carbamic acid esters of phenol, of isomeric cresols and of commercial mixtures thereof and similar aromatic hydroxyl compounds, aliphatic monoalcohols such as methanol, ethanol, propanol, isopropanol, butanol, isobutanol, cyclohexanol, benzyl alcohol and aliphatic diols or polyols such as ethylene glycol and trimethylolpropane.

The O-alkylurethanes may be put into the reaction as such or be prepared in situ by reaction with alcohols. When using O-alkylurethanes for the reaction, up to 50% and preferably 10 to 50% of the isocyanate groups should be present in the O-alkylurethane form.

Instead of the above mentioned isocyanates or polyisocyanate, analogous isothiocyanates and polyisothiocyanates may be used.

α-Halogenated carboxylic acids which are particularly suitable for the process are those corresponding to the formula

and derivatives thereof. In the above formula, Hal denotes halogen, e.g. F, Cl, Br or I, preferably Cl; $R^1$ denotes an aromatic radical containing 5 – 10 carbon atoms which may be substituted, an aliphatic radical containing 1 – 20 carbon atoms, a cycloaliphatic radical containing 5 – 10 carbon atoms or hydrogen. Two radicals R⁴ may together with the α-carbon atoms form a 5-membered to 7-membered cycloaliphatic ring.

The α-halocarboxylic acids and their derivatives used are preferably chloroacetic acid or α-halogenated, e.g. α-chlorinated or α-brominated propionic, butyric, 2-ethylhexanoic, stearic, phenylacetic, diphenylacetic, dimethylacetic, isopropylacetic and cyclohexanoic acid.

Compounds which contain several α-halocarboxylic acid groups as represented by the following formula

are also suitable. In the above formula, R⁶ denotes an aliphatic radical containing 1 – 10 carbon atoms, a cycloaliphatic radical containing 5 – 10 carbon atoms, an aliphatic-aromatic radical containing 6 – 10 carbon atoms, an aromatic radical containing 5 – 10 carbon atoms or a single bond and y represents an integer of from 1 to 3, preferably 2 to 3. These compounds are formed, for example, by α,α'-chlorination or α,α'-bromination of polybasic carboxylic acids such as succinic acid, adipic acid, glutaric acid, sebacic acid or phenylenediacetic acid. The various stereoisomeric forms of dichloro- and dibromosuccinic acids which can be obtained from maleic and fumaric acid are preferred.

To carry out the process, the starting materials may be dissolved in a solvent and then heated to temperatures of about 60° to 350°C. A slow stream of inert gas (e.g. nitrogen or CO₂) is advantageously passed over or through the reaction solution to speed up the removal of the hydrogen halide evolved. The reaction is generally completed when evolution of the hydrogen halide ceases. The reaction lasts from 1 – 50 hours, for example, and is preferably between 1 and 20 hours. The process may be modified by slowly adding one or even both reactants at an elevated temperature, for example 80° to 220°C, to the inert solvent in the reaction vessel or to the other reactants, optionally in solution.

Furthermore, the reactions may be carried out stepwise by first reacting part of the isocyanate with the α-halocarboxylic acid derivatives, e.g. at 80° to 200°C, and then adding the same or one of the other isocyanate components mentioned or the corresponding urethanes, for example at the same temperature range.

Solvents which are inert under the reaction conditions and inert towards the reaction products may be used, for example higher boiling, optionally halogenated aliphatic compounds and aromatic compounds such as paraffin oils, chloroparaffins, chlorobenzene, dichlorobenzenes, nitrobenzene, tetralin, decalin, alkylbenzenes or alkylnaphthalenes and diphenylethers.

Solvents which react with the isocyanates to form so-called masked isocyanates as already described above are, however, preferred and may be used either alone or together with the above mentioned solvents. These reactive solvents are in particular solvents which contain active hydrogen atoms which react with the isocyanates to form derivatives such as urethanes which are easily decomposed back into the original isocyanates by heat. Phenolic solvents are particularly preferred, e.g. phenol, cresols or mixtures thereof.

According to the invention, the reaction may be accelerated with catalysts. The following catalysts, for example, may be used:

1. Tertiary amines, such as triethylamine, tributylamine, N-methyl-morpholine, N-ethyl-morpholine, N-cocomorpholine, N,N,N',N'-tetramethyl-ethylenediamine, 1,4-diaza-bicyclo-(2,2,2,)-octane, N-methyl-N'-dimethylaminoethyl-piperazine, N,N-dimethylbenzylamine, pentamethyldiethylenetriamine, N,N-dimethylcyclohexylamine, N,N,N',N'-tetramethyl-1,3-butanediamine, N,N-dimethyl-β-phenylethylamine, 1,2-dimethylimidazole and 2-methylimidazole;

2. Tertiary amines containing hydrogen atoms which are reactive with isocyanate groups, e.g. triethanolamine, triisopropanolamine, N-methyl-diethanolamine, N-ethyldiethanolamine, N,N-dimethyl-ethanolamine, and their reaction products with alkylene oxides such as propylene oxide and/or ethylene oxide;

3. Silaamines with carbon-silicon bonds (see German patent specification No. 1,229,290), e.g. 2,2,4-trimethyl-2-silamorpholine or 1,3-diethylaminomethyl-tetramethyl-disiloxane;

4. Bases which contain nitrogen such as tetraalkylammonium hydroxides and hexahydrotriazines;

5. Organic metal compounds, in particular of iron, lead and/or tin.

The organic tin compounds used are preferably tin(II) salts of carboxylic acids such as tin(II) acetate, tin(II) octoate, tin(II) ethyl hexoate and tin(II) laurate and the dialkyl tin IV salts of carboxylic acids such as dibutyl tin dichloride, acetate, laurate or maleate or dioctyl tin diacetate. Iron salts such as iron acetylacetonate or iron chloride, lead oxide, lead carbonate or lead carboxylates may also be used.

Other catalysts which may be used according to the invention are described in Kunststoff-Handbuch, Volumn VII, published by Vieweg and Hochtlen, Carl-Hanser-Verlag, Munich 1966, pages 96–102, and in High Polymers, Vol. XVI, Part I (Polyurethanes-Chemistry), published by Saunders and Frisch, Interscience Publishers, New York 1962, pages 129–217.

The compounds obtained according to the invention may be high molecular weight or low molecular weight compounds. This depends mainly on the choice of starting materials and the molar ratios in which they are used.

1. When "monovalent" reactants are used, compounds with only one hydantoin ring are obtained.

2. If one mol of α-halocarboxylic acid is reacted with 2/n mols of a polyiso(thio)cyanate which contains n NCO groups, then a high molecular weight product is obtained if n is greater than 1, preferably n = 2, for example a diisocyanate of formula II and an α-halocarboxylic acid of formula VI yield a high molecular weight product which contains the following recurrent structural unit (VII), of course statistically arranged:

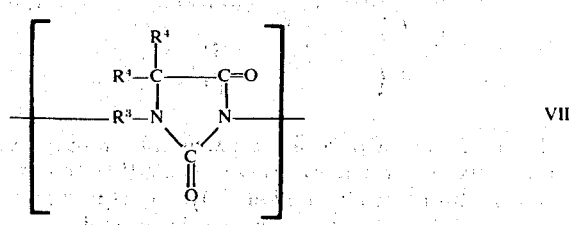

3. If, on the other hand, 1 mol of α-halocarboxylic acid is reacted with 4/n mol of a polyiso(thio)cyanate which contains n NCO groups per molecule, then a product which contains n/2 hydantoin groups per molecule is obtained if n > 1 preferably n = 2. For example, an isocyanate of formula II and halocarboxylic acid of formula VI yield a hydantoin which contains NCO groups as represented by the following formula

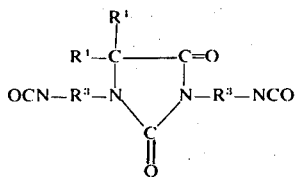    VIII

If the reaction is carried out with a derivative of a diisocyanate, i.e. a so-called masked diisocyanate, or if a phenolic solvent is used, e.g. phenol, cresols or mixtures thereof, then products of the following formula are obtained:

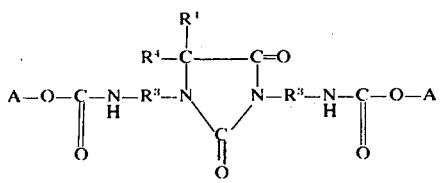    IX in which A denotes an aliphatic or aromatic radical as described above 4. If a polyiso(thio)cyanate which contains n NCO groups per molecule is used in a quantity of between 2/n and 4/n mol for 1 mol of α-halocarboxylic acid, then if n > 1, preferably n = 2, products of the following formula are obtained:

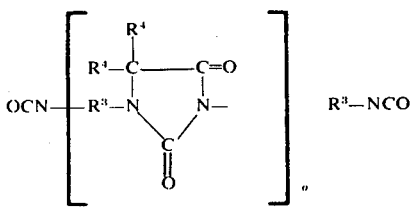    X in which $o$ = 2 to about 200, preferably 2 – 50, and analogously with masked isocyanates or phenolic solvents there are obtained products of the following formula

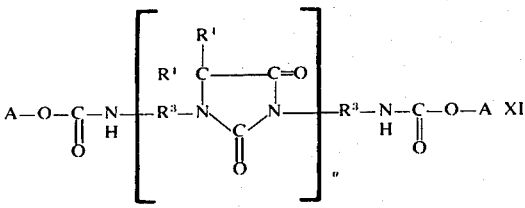    XI

Since the inventive reaction is generally carried out in solvents, the products are also obtained as solutions. These solutions may be used directly as coating materials. When heated to elevated temperatures the products of the invention are converted into hard, non-fusible products. Thus when heated to temperatures of about 100° to 500°C, they give rise to temperature resistant coatings which have extremely high chemical, thermal and physical resistance. It is, therefore, possible to obtain coatings exhibiting outstanding flexibility, surfacehardness, abrasion resistance and resistance to all the conventional solvents such as alcohols, aromatic and aliphatic hydrocarbons, esters, ethers and ketones, and even to water, by applying solutions of the inventive products to heat-resistant supporting bases comprising for example, metals, ceramics, glass or asbestos fibres, or fabrics made from such fibres, or even to other adequately temperature-resistant synthetics, and then stoving at elevated temperatures.

The isocyanate or isothiocyanate groups still left in the products would be expected to form high molecular weight materials by chain lengthening or cross-linking although cross-linked substances may also be formed from isocyanates which have a valency higher than 2 or from the polyfunctional α-halocarboxylic acids already mentioned above, in which the proportion of cross-linking components may vary within very wide limits. Thus from 1 mol of α,α'-dichlorosuccinic acid and 4 mols of 4,4'-diisocyanato-diphenylmethane there is obtained an oligomer which contains two hyantoin rings and 4 optionally masked NCO groups and in which the hydantoin rings are linked through the 5,5'-position, where as in linear polymers which have the mixture indicated in equation 2 the addition of only 0.2% of a cross-linking component is enough to form isoluble polymers. The cross-linking component may in a stoichiometric reaction mixture therefore advantageously consist of an iso(thio)cyanate which is more than difunctional or an α-halocarboxylic acid which is more than monofunctional. The amount of this cross-linking component which may be the isocyanate already present or the α-halocarboxylic acid already present may be 0.2 to 50 mols percent and is preferably 0.5 to 10 mols percent. The resulting synthetic resins, coatings or sheet structures have excellent flexibility and surface hardness as well as excellent abrasion resistance and resistance to all the usual solvents such as alcohols, aromatic and aliphatic hydrocarbons, esters, ethers and ketones as well as water.

The outstanding properties of the inventive products which guarantee synthetic resins, coatings or structures of excellent flexibility, surface-hardness and high temperature resistance, remain largely unaffected, or can be varied as required, when other polymers known per se are jointly used, for example, polyesters, polyamides, polyurethanes, polyolefins, polyacetals, polyepoxides, polyimides, polyamide-imides, polyimino-polyesters and polyimide isocyanates. The quantities in which these polymers are used will largely depend upon the properties required of the end product and the weight ratio of the polymers of the invention to the known polymers may conveniently vary from 10 : 90 to 90 : 10. They are preferably mixed in a weight ratio of 30 : 70 to 70 : 30. These known polymers may be added to the polyhydantoins or may even be incorporated in them by polymerisation and condensation.

There should also be particularly mentioned the modification which is obtained by adding polyesters which contain reactive hydroxyl groups. When these polyesters are used with high or low molecular weight compounds according to this invention which contain masked or free NCO groups as for instance described in the formulae VIII – XI they cause chain lenghtening or cross-linking of the molecules by way of urethane groups, either directly or after removal of the masking group. Coatings obtained from these polymers have also an excellent flexibility and surface-hardness and are high temperature resistant.

Suitable polyesters containing hydroxyl groups include the known types which can be obtained by routine methods from polycarboxylic acids, for example succinic acid, adipic acid, sebacic acid, phthalic acid, isophthalic acid, terephthalic acid or maleic acid and polyalcohols, for example glycol, diethylene glycol, triethylene glycol, propylene glycol, dipropylene glycol, glycerol, 1,1,1-tri-methylol propane or pentaerythritol.

EXAMPLE 1

900 Parts by weight of m-cresol are heated to 120°C and 375 parts by weight of 4,4'-diisocyanato diphenylmethane are added in the course of 2 hours at a rate adjusted to the exothermic reaction. 71 Parts by weight of chloroacetic acid are then added at the same temperature. Evolution of carbon dioxide takes place at this stage. The reaction mixture is then slowly heated to about 185°C and kept at this temperature while anhydrous nitrogen is passed through until evolution of HCl ceases (in about 15 hours). 1278 Parts by weight of a solution in m-cresol of a polyhydantoin of the following structure is obtained. This solution has a concentration of 30%, based on the free isocyanate content. The viscosity of this 30% solution is 9243 $cP_{25°}$. The chlorine content is below 0.2%. The presence of the hydantoin ring structure is confirmed by the typical IR absorption at 1755 $cm^{-1}$.

characteristic absorption at 1755 $cm^{-1}$ in the IR spectrum.

EXAMPLE 3

770 Parts by weight of m-cresol are reacted with 375 parts by weight of 4,4'-diisocyanato diphenylmethane and 94.5 parts by weight of chloroacetic acid by the method described in Example 1, first at 120°C and then for 15 hours at 185°C. 1102 Parts by weight of a 35% solution (based on the free isocyanate) of the oligohydantoin is obtained. Its theoretical NCO content is 3.8% and the hydantoin structure is confirmed by the absorption at 1755 $cm^{-1}$. $cP_{25°}=90000$.

The hydantoin can be precipitated from the solution with methanol or an equal number of parts of acetone by the method indicated in Example 2.

500 parts by weight of the above obtained 35% solution of an oligohydantoin in cresol are mixed with a solution of 567 parts by weight of a polyester obtained from 1,6 mol terephthalic acid dimethylester, 1,2 mol ethylene glycol and 0,8 mol glycerine and having 6% by weight OH groups in 1300 parts by weight cresol at 50°C.

A homogeneous solution having a viscosity of 8350 $cP_{25}$ is obtained. This solution is applied to a metal sheet and stoved for 30 minutes at 240°C and for 10 minutes at 300°C to a hard, brilliant lacquer film having a high resistance to various organic solvents.

EXAMPLES 4 – 6

In accordance with the method described in Example 1, 275 (4), 262.5 (5) or 252.5 (6) parts by weight of 4,4'-diisocyanatodiphenylmethane are added to 740

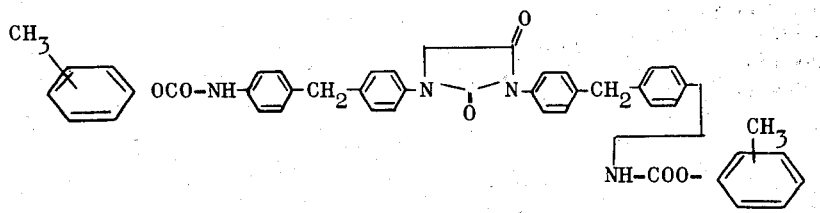

500 parts by weight of the above obtained 30% solution of the hydantoin compound in cresol is mixed with a solution of 750 parts by weight of a polyester obtained from 1,6 mol terephthalic acid dimethylester, 1,2 mol ethylene glycol and 0,8 mol glycerine in 1300 parts by weight cresol at 50°C. A homogeneous solution having a viscosity of 5120 $cP_{25°}$ is obtained.

This solution is applied to a metal sheet and stoved for 30 minutes at 240°C and for 10 minutes at 300°C to a clear lacquer film of a very high surface resistance and resistance to various organic solvents.

EXAMPLE 2

200 Parts by weight of the solution obtained according to Example 1 is introduced with vigorous stirring into about 1500 parts by weight of methanol. The resulting precipitate is washed with methanol and dried under vacuum at 80°C. 42.5 Parts by weight of the hydantoin-isocyanate derivative described in Example 1 is obtained. It has a softening point of about 162° – 165°C and its hydantoin structure is confirmed by the (4) or 710 (5 + 6) parts by weight of m-cresol, and 94.5 parts by weight of chloroacetic acid are then added and the reaction mixture is kept at 185°C for about 25 hours, until evolution of HCl ceases. The following solutions are obtained:

| Example 4 | 1026 parts by weight | $cP_{25°}$ | 4840 |
| Example 5 | 981 parts by weight | $cP_{25°}$ | 5100 |
| Example 6 | 973 parts by weight | $cP_{25°}$ | 3700 |

The products contain less than 0.2% of chlorine and have the typical hydantoin band at 1755 $cm^{-1}$.

EXAMPLE 7

174 Parts by weight of tolylene diisocyanate (isomeric mixture 2,4 : 2.6 = 80 : 20) are added dropwise to 500 parts by weight of m-cresol at 150°C, and 47 parts by weight of chloroacetic acid are then introduced. 678 Parts by weight of the solution in cresol of a hydantoin diisocyanate which has the following theoretical structure

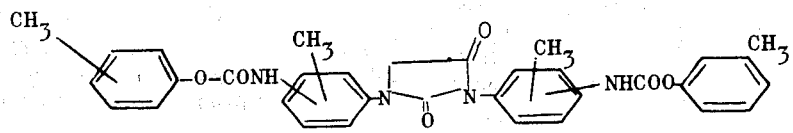

are obtained after 15 hours heating at 185°C. The product has a viscosity of $cP_{25}° = 19620$ and a chlorine content of 0.6%. The hydantoin absorption in the IR spectrum is seen at 1755 cm$^{-1}$.

EXAMPLE 8

300 Parts by weight of phenol are reacted with 125 parts by weight of 4,4'-diisocyanate diphenylmethane and 27 parts by weight of 2-chloropropionic acid at 120° and 185°C by the method described in Example 1 and 433 parts by weight of a hydantoin solution which contains 0.35% of chlorine are obtained.

EXAMPLE 9

137.5 Parts by weight of 4,4'-diisocyanate diphenylmethane, 6.9 parts by weight of 2,3-dibromosuccinic acid (or the equivalent quantity of 2,3-dichlorosuccinic acid) and 42.3 parts by weight of chloroacetic acid are introduced into 370 parts by weight of cresol at 120°C. 516 Parts by weight of a slightly branched hydantoin are obtained after 15 hours at 200°C. $cP_{25}°$ ₍=5450, 0.2% chlorine, IR 1755 cm$^{-1}$.

EXAMPLE 10

222 Parts by weight of isophorone diisocyanate are heated to 180°C, and 47 parts by weight of chloroacetic acid are introduced at this temperature. Evolution of $CO_2$ and HCl takes place. After 12 hours at 180° to 185°C while inert gas (nitrogen) is passed through, 230 parts by weight of a hard resin which contains 13.5% of free isocyanate and 0.35% of chlorine are obtained. The IR spectrum shows the typical hydantoin absorption at 1755 cm$^{-1}$.

EXAMPLE 11

710 parts by weight of cresol are heated to 80°C and 200 parts by weight of 4,4'-diisocyanato-diphenylmethane and 65 parts by weight of a higher homologous polyphenylene methylene polyisocyanate (31.6% NCO, approximately 30% of trivalent and higher valent compounds, $cP_{25}°$ ₍ = 110) and 94.5 parts by weight of chloroacetic acid are introduced at this temperature. After about 12 hours at 185°C, the product still contains less than 0.2% of chlorine and has a viscosity of $cP_{25}°$ ₍=6430. The hydantoin structure is conformed by the IR band at 1755 cm$^{-1}$.

EXAMPLE 12

160 Parts by weight of m-phenylene diisocyanate followed by 95 parts by weight of chloroacetic acid are introduced into 410 parts by weight of m-cresol at 120°C. The reaction mixture is heated to 185°C within 3 hours and kept at a temperature of 185°-200°C for 15 hours while nitrogen is passed through. Approximately 580 parts by weight of an approximately 30% polyhydantoin solution in cresol which has a chlorine content below 0.2% and shows the typical hydantoin absorption at 1755 cm$^{-1}$ remains behind. The viscosity of the solution is about 77170 $cP_{25}°$ ₍.

The cresol solution is precipitated by pouring it into about 4000 parts by weight of methanol. After suction filtration and drying, 162 parts by weight of polyhydantoin containing 0.3% of Cl and 15.3% of N are obtained.

EXAMPLE 13

249 Parts by weight of the polyhydantoin are obtained by the method described in Example 12 from 625 parts by weight of m-cresol, 252 parts by weight of 4,4'-diisocyanatodiphenylether and 95 parts by weight of chloroacetic acid. At the end of the reaction, the cresol solution contains less than 0.2% of chlorine and has a viscosity of 30520 $cP_{25}°$ ₍. The product is isolated from this solution by precipitation with methanol. The polyhydantoin contains 9.5% of N and less than 0.2% of Cl and its structure is confirmed by the IR spectrum.

EXAMPLES 14 – 17

The catalyst indicated below is added to 655 parts by weight of cresol, 262.5 parts by weight of 4,4'-diisocyanato diphenylmethane followed by 94.5 parts by weight of distilled chloroacetic acid are then added at 100°C. The reaction mixture is then heated to 185°C for 8 hours while an inert gas is passed through. The theroetical yield is obtained. The hydantoin structure is confirmed by the IR absorption band at 1755 cm$^{-1}$.

EXAMPLE 14

0.44 Parts by weight of iron acetyl acetonate: $cP_{25}°$ ₍=12208.

EXAMPLE 15

0.075 parts by weight PbO: $cP_{25}°$ ₍=9025.

EXAMPLE 16

0.177 parts by weight dibutyl tin dichloride: $cP_{25}°$ ₍=15700.

EXAMPLE 17

0.24 Parts by weight of tin(II) octoate: $cP_{25}°$ ₍=14475.

EXAMPLE 18

425 Parts by weight of cresol are heated to 180°–185°C after the addition of 0.44 parts by weight of iron acetyl acetonate, and the following two solutions are then added simultaneously from separate dropping funnels:

a. A solution of 262.5 parts by weight of 4,4'-diisocyanatodiphenylmethane in 150 parts by weight of toluene and b. a solution of 94.5 parts by weight of chloroacetic acid in 230 parts by weight of cresol. The solutions are added dropwise in the course of 2 hours. The toluene distills off as soon as it is added and at the same time $CO_2$ and HCl are evolved. The reaction mixture is kept at 185°C for a further 8 hours. The product obtained corresponds to the polyhydantoin solution prepared according to Example 14.

An analogous solution is obtained when 94.5 parts by weight of chloroacetic acid in 655 parts by weight of cresol are introduced into a reaction vessel and only the isocyanate solution is added dropwise at 180°C.

EXAMPLE 19

0.64 Parts by weight of iron acetylacetonate are added to 580 parts by weight of cresol and a solution of 375 parts by weight of 4,4'-diisocyanatodiphenylmethane in 200 parts by weight of toluene is then added dropwise at 70°C. The reaction mixture is heated to 100°C, 94.5 parts by weight of distilled chloroacetic acid are then added, and the reaction mixture is kept at 180°C for 8 hours. The approximately 40% solution of hydantoin in cresol is identified by the IR absorption of the hydantoin group at 1755 cm⁻¹.

EXAMPLE 20

355 Parts by weight of m-cresol and 0.07 parts by weight of dibutyl tin dichloride are heated to 120°C and 131.2 parts by weight of 4,4'-diisocyanatodiphenylmethane followed by 94.5 parts by weight of chloroacetic acid are introduced. In addition, a solution of 300 parts by weight of m-cresol, 75 parts by weight of anhydrous n-butanol and 131.3 parts by weight of 4,4'-diisocyanato-diphenylmethane is prepared separately at 120°C. This solution is introduced into the first solution in the course of 2 to 3 hours at 150°C. The combined solutions are then heated under reflux conditions for about 15 hours to distill off the butanol, and HCl evolves at the same time (approximately 190°C). A polyhydantoin solution analogous to that obtained in Example 16 and having a viscosity of 7500 cP$_{25}$° $c$ is obtained in quantitative yield.

EXAMPLE 21

A solution prepared in a manner analogous to Example 20 from 355 parts by weight of m-cresol, 0.07 parts by weight of dibutyl tin dichloride, 137.5 parts by weight of 4,4'-diisocyanatodiphenylmethane and 94.5 parts by weight of chloroacetic acid is heated to 160°C and a solution of 199 parts by weight of 4,4'-bis-n-butoxycarbonylamino-diphenylmethane in 300 parts by weight of cresol is then introduced dropwise. After 15 hours' heating at 190°C, a polyhydantoin solution corresponding to that of Example 20 is obtained.

EXAMPLE 22

262.5 Parts by weight of 4,4'-diisocyanatodiphenylmethane followed by 94.5 parts by weight of chloroacetic acid are added to 655 parts by weight of m-cresol, 0.07 parts by weight of dibutyl tin dichloride, 6.2 parts by weight of ethylene glycol and 30 parts by weight of isopropanol at 120°C. A solution of polyhydantoin is obtained in a manner analogous to Example 20 by heating to about 190°C for about 15 hours.

We claim:
1. A process for the preparation of a hydantoin which comprises reacting at a temperature of 50° to 350°C.
   a. at least one compound of the formula

$$R^3(-NCX)_z$$

wherein X is O or S;
   z is an integer of from 2 to 3 and $R^3$ is an optionally substituted aliphatic radical containing 1–20 carbon atoms, an optionally substituted aromatic radical containing 5–12 carbon atoms, a cycloaliphatic radical containing 5–12 carbon atoms, an aliphatic-aromatic radical containing 6–20 carbon atoms or an aromatic or cycloaliphatic heterocyclic radical containing 5–12 ring atoms which contains or is substituted by hetero atoms such as N, O or S, with
   b. at least one α-halocarboxylic acid selected from the group consisting of

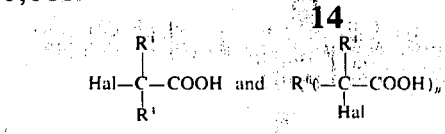

wherein Hal is halogen; $R^4$ is an optionally substituted aromatic radical containing 5–10 carbon atoms, an aliphatic radical containing 1–20 carbon atoms, a cycloaliphatic radical containing 5–10 carbon atoms, hydrogen or two radicals $R^4$ taken together with the carbon atom to which they are attached form a cycloaliphatic ring of 5–7 ring members; $R^6$ is an aliphatic radical containing 1–10 carbon atoms, a cycloaliphatic radical containing 5–10 carbon atoms, an aliphatic-aromatic radical containing 6–10 carbon atoms or an aromatic radical containing 5–10 carbon atoms and $y$ is an integer of from 1 to 3.

2. The process as claimed in claim 1 wherein the reaction is carried out in a phenolic solvent or in the presence of an aliphatic alcohol or polyol.

3. The process as claimed in claim 1 wherein up to 50% of (a) is replaced by a corresponding O-alkylurethane.

4. The process as claimed in claim 1 wherein the reaction is carried out in the presence of an organic iron, lead or tin compound or iron chloride, lead oxide or lead carbonate.

5. The process as claimed in claim 1 wherein the reaction is carried out in the presence of a tertiary amine.

6. The process as claimed in claim 1 wherein 1 mol of (b) is reacted with 2/z mol of (a).

7. The process as claimed in claim 1 wherein 1 mol of (b) is reacted with 4/z mol of (a).

8. The process as claimed in claim 1 wherein 1 mol of (b) is reacted with from 2/z to 4/z mol of (a).

9. The process as claimed in claim 1 wherein (a) is tolylene diisocyanate, m-phenylene diisocyanate, polyphenylmethylene-polyisocyanate, 4,4-diisocyanato-diphenylmethane, 4,4-diisocyanato-diphenylether, 4,4-diisocyanato-diphenyldimethylmethane, p-phenylene diisocyanate or hexamethylene diisocyanate.

10. The process as claimed in claim 1 wherein (b) is chloroacetic acid, α-chlorinated or α-brominated propionic, butyric, 2-ethylhexanoic, stearic, phenylacetic, diphenylacetic, dimethylacetic, isopropylacetic, cyclohexanoic acid, α,α'-chlorinated or α,α'-brominated succinic, adipic, glutaric, sebacic or phenylene diacetic acid.

11. An oligohydantoin or polyhydantoin containing in statistical arrangement the structural unit

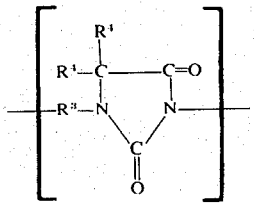

wherein $R^4$ is hydrogen, an optionally substituted aromatic radical containing 5–10 carbon atoms, an aliphatic radical containing 1–20 carbon atoms, a cycloaliphatic radical containing 5–10 carbon atoms or the two radicals $R^4$ taken together with the carbon atom to which they are attached from a cycloaliphatic ring of 5–7 ring members and $R^3$ is an optionally substituted aromatic radical containing 5–12 carbon atoms.

12. An oligohydantoin of claim 11 which contains isocyanate groups of the formula
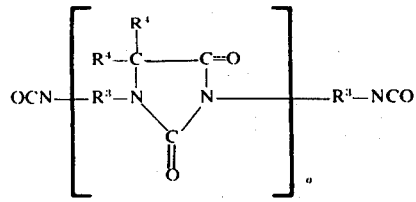
wherein $o$ is an integer of from 2 to 200.
13. An oligohydantoin of claim 11 which contains masked isocyanate groups of the formula
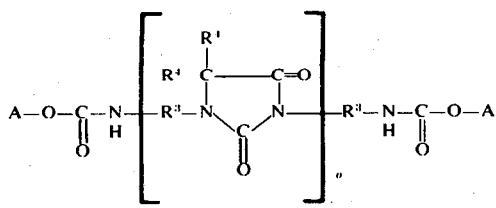
wherein A is an aliphatic or aromatic radical and $o$ is an integer of from 2–200.
* * * * *